United States Patent [19]

Sohn et al.

[11] Patent Number: 4,925,478
[45] Date of Patent: May 15, 1990

[54] NOVEL QUINOLINOXY COMPOUNDS, A PROCESS FOR THEIR PREPARATION, AND THEIR USE AS ANTIDOTES

[75] Inventors: Erich Sohn, Esslingen; Reinhard Handte, Gablingen; Hilmar Mildenberger, Kelkheim; Klaus Bauer, Hanau; Hermann Bieringer, Eppstein/Taunus, all of Fed. Rep. of Germany

[73] Assignee: Hoechst Aktiengesellschaft, Frankfurt am Main, Fed. Rep. of Germany

[21] Appl. No.: 76,111

[22] Filed: Jul. 21, 1987

[30] Foreign Application Priority Data

Jul. 23, 1986 [DE] Fed. Rep. of Germany ....... 3624859

[51] Int. Cl.$^5$ ..................... A01N 43/42; C07D 215/26
[52] U.S. Cl. ............................................ 71/90; 71/92; 544/354; 546/178
[58] Field of Search ...................... 546/178; 71/92, 90; 544/354

[56] References Cited

U.S. PATENT DOCUMENTS

| | | | |
|---|---|---|---|
| 3,351,525 | 11/1967 | Hodel | 546/178 |
| 4,602,932 | 7/1986 | Handte et al. | 71/94 |
| 4,749,406 | 6/1988 | Martin | 71/94 |

FOREIGN PATENT DOCUMENTS 0138773 10/1984 European Pat. Off.
0154153 1/1985 European Pat. Off.
0254222 1/1988 European Pat. Off. ............ 546/178

OTHER PUBLICATIONS

Oguchi, et al., "Chemical Abstracts", vol. 98, 1983, col. 98:53729z.
Martin, "Chemical Abstracts", vol. 103, 1985, col. 103:215201x.
Sohn, et al., "Chemical Abstracts", vol. 108, 1988, col. 108:186596a.

Primary Examiner—Richard L. Raymond
Assistant Examiner—James H. Turnipseed
Attorney, Agent, or Firm—Curtis, Morris & Safford

[57] ABSTRACT

Compounds of the formula

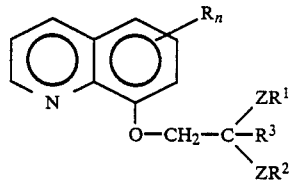

in which $R_n$ denotes hydrogen, halogen or alkyl, Z denotes oxygen or sulfur, $R^1$ and $R^2$, independently of one another, denote hydrogen, alkyl, alkoxyalkyl, haloalkyl or phenalkyl, or, together, denote a (optionally substituted) $C_2$–$C_4$-alkylene bridge, and $R^3$ denotes hydrogen or alkyl, are effective antidotes for protecting crop plants against phytotoxic side effects of herbicides.

12 Claims, No Drawings

NOVEL QUINOLINOXY COMPOUNDS, A PROCESS FOR THEIR PREPARATION, AND THEIR USE AS ANTIDOTES

The present invention relates to novel quinolinoxy compounds for protecting crop plants against damaging side effects of argricultural chemicals.

On use of plant-treatment agents, in particular on use of herbicides, undesired damage can arise in the crop plants treated. Particularly on application of herbicides after emergence of the crop plants, the need often exists, therefore, to prevent the risk of possible phytotoxicity by adding so-called "antidotes" or "safeners". A number of quinolinoxy compounds have already been described as such antidotes (EP-A 94,349 and EP-A 152,006).

Surprisingly, it has now been found that the quinolinoxy compounds of the formula I have superior plant-protecting properties in various crops compared to the state of the art.

The present invention therefore relates to compounds of the formula

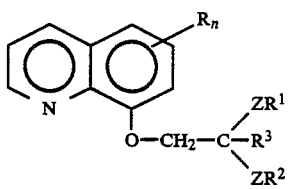

I a process for their preparation, and their use as safeners for herbicides, the individual radicals having the following meaning:

R, in each case independently of one another, denotes halogen or $(C_1-C_4)$alkyl, Z, in each case independently of one another, denotes O or S, $R^1$ and $R^2$, independently of one another, denotes H, $(C_1-C_8)$-alkyl, $(C_3-C_8)$-alkenyl, $(C_1-C_4)$alkoxy-$(C_1-C_4)$alkyl, $(C_1-C_{12})$haloalkyl having up to 17 halogen atoms, $(C_3-C_{12})$haloalkenyl having up to 17 halogen atoms or phenyl-$(C_1-C_2)$alkyl, or $R^1$ and $R^2$ together denote a di-, tri- or tetramethylene chain which is optionally substituted by up to two $(C_1-C_8)$-alkyl, $(C_1-C_4)$haloalkyl or $(C_1-C_4)$alkoxy-$(C_1-C_4)$-alkyl groups and/or by an oxo group, $R^3$ denotes H or $(C_1-C_4)$alkyl, and n denotes 0, 1, 2 or 3, and the salts and N-oxides thereof.

The compounds are novel, with one exception. Only α-quinolyloxy-acetaldehyde diethyl acetal is known (Tokyo Gakugei Daigaku Kiyo, Dai-4-bumon 34 (1982), 55-59).

In the definition of R, "halogen" preferably denotes chlorine or bromine, whereas "halogen" in $R^1$ and $R^2$ preferably represents fluorine or chlorine.

R=$(C_1-C_4)$alkyl is preferably methyl.

$R^1$ and $R^2$ can adopt, for example, the following meanings: methyl, ethyl, n-propyl, n-butyl, i-butyl, i-propyl, n-amyl, n-hexyl, n-heptyl, n-octyl, allyl, methallyl, crotyl, 6-octenyl, $CF_3$, $CCl_3$, $CCl_2CH_3$, $CHCl-CCl_3$, $CHF-CCl_3$, $CHCl-CCl_2-CH_3$, $CCl_2-CH=CF_2$, benzyl or phenethyl.

Particularly preferred compounds of the formula I are those in which R denotes halogen, Z denotes oxygen, $R^1$ and $R^2$ denote $(C_1-C_4)$alkyl or $(C_1-C_2)$alkoxy-$(C_1-C_2)$-alkyl, $R^3$ denotes hydrogen and n denotes 1 or 2.

Organic and inorganic acids are taken to mean those which are capable of protonating the compounds of the formula I, such as, for example, hydrochloric acid, sulfuric acid, phosphoric acid, nitric acid, oxalic acid, trichloroacetic acid, and alkyl- and arylsulfonic acids.

The application furthermore relates to a process for the preparation of the compounds of the formula (I), wherein compounds of the formula II

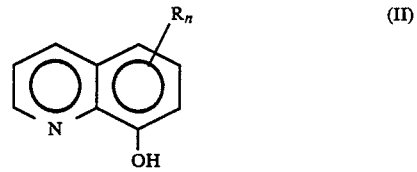

are reacted with compounds of the formula (III)

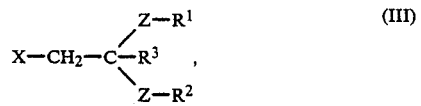

in which the radicals have the abovementioned meaning and X represents a leaving group, and, if desired, the acetals of the formula (I) thus obtained are converted by transacetalization, into other derivatives of the formula (I) or compounds of the formula I are converted into their salts or N-oxides.

The compounds of the formula (II) are usually reacted with compounds of the formula (III) at temperatures between 0° and 150° C., preferably between 50° and 100° C., advantageously in the presence of a solvent and an auxiliary base. Suitable solvents are, for example, lower alcohols, benzene, toluene or dioxane; suitable auxiliary bases are $K_2CO_3$ or $Na_2CO_3$. For some derivatives of the formula (I), it is advantageous to alkylate the compounds of the formula (II) using an easily accessible compound of the formula (III) and then to convert them, by transacetalization, into the desired compound of the formula (I), for example by heating with a suitable alcohol, dialcohol or mercaptan in excess or using an inert solvent, preferably in the presence of an acidic catalyst, such as $H_2SO_4$, p-toluenesulfonic acid or trifluoromethanesulfonic acid, in an organic solvent. If desired, the compound of the formula (I) can be converted into its N-oxides or into its salts by conventional methods (cf. J. Org. Chem. 18, 534 (1953)).

The compounds of the general formula (I) are distinguished by the fact that they are applied in low, i.e. subtoxic, concentrations in combination with herbicides and are then capable of antagonizing, i.e. completely negating, damaging side effects of the latter without impairing the herbicidal activity thereof. By this means, the area of use of conventional plant-protecting agents can be very considerably broadened. The invention therefore also relates to a process for protecting crop plants against phytotoxic side effects of plant-protecting agents, in particular herbicides, wherein the plants, parts of plants or nutritive substrata of plants are treated with a compound of the formula I before, after or simultaneously with the plant-protecting agents.

Herbicides whose phytotoxic side effects can be reduced by means of compounds of the formula I are, for example, carbamates, thiocarbamates, haloacetanilides, substituted phenoxy-, naphthoxy- and phenoxyphenoxycarboxylic acid derivatives and also heteroaryloxyphenoxycarboxylic acid derivatives, such as quinolyloxy-, quinoxalyloxy-, pyridyloxy-, benzoxazolyloxy-, benzothiazolyloxy-phenoxycarboxylic acid esters, and furthermore dimedone oxime derivatives. Phenoxy- and heteroaryloxyphenoxy-carboxylic acid esters are preferred herein.

Herbicides from the following classes may be mentioned as examples, without representing a limitation thereby:

(A) Herbicides from the class of the $(C_1-C_4)$-alkyl, substituted $(C_1-C_4)$-alkyl, $(C_2-C_4)$alkenyl and $(C_3-C_4)$-alkynyl phenoxyphenoxy- and heteroaryloxyphenoxycarboxylates, such as
  1. Methyl 2-(4-(2,4dichlorophenoxy)-phenoxy)-propionate (diclofop-methyl),
  2. Methyl 2-(4-(4-bromo-2-chlorophenoxy)-phenoxy)-propionate,
  3. Methyl 2-(4-(4-trifluoromethylphenoxy)-phenoxy)-propionate,
  4. Methyl 2-(4-(2-chloro-4-trifluoromethylphenoxy)-phenoxy)-propionate,
  5. Methyl 2-(4-(2,4-dichlorobenzyl)-phenoxy-propionate,
  6. Ethyl 4-(4-(4-trifluoromethylphenoxy)-phenoxy)-pent-2-enoate,
  7. Ethyl 2-(4-(3,5-dichloropyridyl-2-oxy)-phenoxy)-propionate,
  8. Propargyl 2-(4-(3,5dichloropyridyl-2-oxy)-phenoxy)-propionate,
  9. Ethyl 2-(4-(6-chlorobenzoxazol-2-yl-oxy)-phenoxy)-propionate (fenoxaprop-ethyl),
  10. Ethyl 2-(4-(6-chlorobenzothiazol-2-yloxy)-phenoxy)-propionate,
  11. Methyl 2-(4-(3-chloro-5-trifluoromethyl-2-pyridyloxy)-phenoxy)-propionate,
  12. Butyl 2-(4-(5-trifluoromethyl-2-pyridyloxy)-phenoxy)-propionate (fluazifop-butyl),
  13. Ethyl 2-(4-(6-chloro-2-quinoxalinyloxy)-phenoxy)-propionate,
  14. Trimethylsilylmethyl 2-(4-(3,5-dichloropyridyl-2-oxy)-phenoxy)-propionate,
  15. Ethyl 2-(4-(3-chloro-5-trifluoromethoxy-2-pyridyloxy)-phenoxy)-propionate, (B) Chloroacetanilides, such as
  1. N-methoxymethyl-2,6-diethyl-chloroacetanilide,
  2. N-(3'-methoxyprop-2'-yl)-2-methyl-6-ethyl-chloroacetanilide,
  3. N-(3-methyl-1,2,4-oxdiazol-5-ylmethyl)-2,6-dimethyl-chloroacetanilide, (C) Thiocarbamates, such as
  1. S-ethyl N,N-dipropylthiocarbamate or
  2. S-ethyl N,N-diisobutylthiocarbamate, (D) Dimedone derivatives, such as
  1. 2-(N-ethoxybutyrimidoyl)-5-(2-ethylthiopropyl)-3-hydroxy-2-cyclohexen-1-one,
  2. 2-(N-ethoxybutyrimidoyl)-5-(2-phenylthiopropyl)-3-hydroxy-2-cyclohexen-1-one or
  3. 2-(1-allyloxyiminobutyl)-4-methoxycarbonyl-5,5-dimethyl-3-oxocyclohexenol,
  4. 2-(N-ethoxypropionamidoyl)-5-mesityl-3-hydroxy-2-cyclohexen-1-one, and
  5. 2-(N-ethoxybutyrimidoyl)-3-hydroxy-5-(thian-3-yl)-2-cyclohexen-1-one.

In these cases, the mixtures of enantiomers in any ratios and the pure antipodes are covered.

The antidote:herbicide amount ratio can vary within broad limits between 0.01 and 10 parts of antidote per part of herbicide. The ideal amounts of each of herbicide and antidote depend on the type of herbicide or antidote used and on the species of the plant crop to be treated, and can be determined from case to case by appropriate experiments.

The main areas of application for the use of safeners are, above all, cereal crops (wheat, rye, barley and oats), rice, corn, sorghum, but also cotton, sugarbeet, sugar cane and soybean.

Depending on their properties, the safeners can be used for pretreatment of the seed of the crop plant (dressing of the seed), introduced into the seed furrows before sowing, or used together with the herbicide before or after emergence of the plants. Pre-emergence treatment includes treatment of the cultivated area before sowing and treatment of the cultivated areas after sowing, but before growth has occurred.

In principle, the antidote can be applied before, after or simultaneously with a herbicide, but simultaneous application in the form of tank mixes or, if appropriate, ready mixes is preferred.

For application, the compounds of the formula I can be formulated, with conventional formulation auxiliaries, into dusting agents, wettable powders, dispersions, emulsion concentrates granules or microgranules which contain the active compound in concentrations of 2–80% and are either used as such (dusting agents and pellets) or are dissolved or dispersed in a solvent (water) before application.

Wettable powders are preparations, uniformly dispersible in water, which contain, besides the active ingredient and, if appropriate, in addition to a diluent or inert material, wetting agents, for example polyoxyethylated alkylphenols, polyoxyethylated fatty alcohols, alkyl or alkylphenyl sulfonates, and a dispersing agent, for example sodium ligninsulfonate, sodium 2,2'-dinaphthylmethane-6,6'-disulfonate, sodium dibutylnaphthalenesulfonate, or sodium oleoylmethyltaurinate. Preparation is carried out in a conventional fashion, for example by grinding and mixing the components.

Emulsifiable concentrates are prepared, for example, by dissolving the active ingredient in an inert organic solvent, for example butanol, cyclohexanone, dimethylformamide, xylene or higher-boiling aromatics or hydrocarbons, with addition of one or more emulsifiers. In the case of liquid active ingredients, the solvent part can be omitted completely or partly. As emulsifiers, the following can be used, for example: calcium salts of alkylarylsulfonic acids, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensatin products, fatty alcohol/propylene oxide/ethylene oxide condensation products, alkyl polyglycol ethers, sorbitan fatty acid esters, polyoxyethylene sorbitan fatty acid esters or polyoxyethylene sorbitol esters.

Dusting agents can be obtained by grinding the active ingredient with finely divided solid substances, for example talcum, natural clays, such as kaolin, bentonite, pyrophillite or diatomaceous earth.

Granules can be prepared either by atomizing the active ingredient onto adsorptive, granulated inert material or by applying active ingredient concentrates onto the surface of carrier materials such as sand or kaolinites, or of granulated inert material, by means of adhesives, for example polyvinyl alcohol or sodium polyacrylate, or alternatively mineral oils. Suitable active ingredients can also be granulated in the fashion which is conventional for the preparation of fertilizer granules, if desired mixed with fertilizers.

In wettable powders, the active ingredient concentration is, for example, about 10 to 90% by weight, the remainder to 100% by weight comprising conventional formulation components. In the case of emulsifiable concentrates, the active ingredient concentration can be about 10 to 80% by weight. Dust-form formulations usually contain 5 to 20% by weight of active ingredient, and sprayable solutions about 2 to 20% by weight. in the case of granules, the active ingredient content depends partly on whether the active compound is present in liquid or solid form and on which granulation auxiliaries, fillers etc. are used.

In addition, the active ingredient formulations mentioned contain, if appropriate, the adhesives, wetting agents, dispersants, emulsifiers, penetrants, solvents, fillers or excipients which are conventional in each case.

For application, the concentrates, present in commercially available form, are diluted, if appropriate, in a conventional fashion, for example using water in the case of wettable powders, emulsifiable concentrates, dispersions and, in some cases, also in the case of microgranules. Dust-form and granulated formulations and also sprayable solutions are usually not further diluted with additional inert substances before application.

A. FORMULATION EXAMPLES (a) A dusting agent is obtained by mixing 10 parts by weight of safener and 90 parts by weight of talcum or inert material and comminuting in a hammer mill.

(b) A wettable powder which is easily dispersible in water is obtained by mixing 25 parts by weight of safener, 64 parts by weight of kaolin-containing quartz as inert material, 10 parts by weight of potassium ligninsulfonate and 1 part by weight of sodium oleylmethyltaurinate as wetting and dispersing agent, and grinding in a pin disk mill.

(c) A dispersion concentrate which is easily dispersible in water is obtained by mixing 20 parts by weight of safener with 6 parts by weight of alkylphenol polyglycol ether (Triton X 207), 3 parts by weight of isotridecanol polyglycol ether (8 EO) and 71 parts by weight of paraffinic mineral oil (boiling range, for example, about 255° to above 377° C.), and grinding in a ball mill to a fineness of below 5 microns.

(d) An emulsifiable concentrate is obtained from 15 parts by weight of safener, 75 parts by weight of cyclohexanone as solvent and 10 parts by weight of oxyethylated nonylphenol as emulsifier.

B. PREPARATION EXAMPLES:

Example 1

5-Chloroquinol-8-yloxy-acetaldehyde diethyl acetal (1)

180 g of 5-chloro-8-hydroxyquinoline, 237 g of 2-bromoacetaldehyde diethyl acetal and 200 g of potassium carbonate are stirred for 4 h at 120° C. in 800 ml of dimethylformamide. After cooling, the mixture is poured into 2.5 liters of water, and the product is filtered off under suction and dried in vacuo, melting point 51°–53° C.

Example 2

5-Chloroquinol-8-yloxy-acetaldehyde di(2,2,3,4,4,4-hexafluorobutan-1-yl) acetal (2)

30 g of (1) are dissolved in 100 ml of 2,2,3,4,4,4,-hexafluorobutan-1-ol, 10 ml of sulfuric acid are added, and the mixture is stirred for 6 h at 60° C. The solvent is then removed by distillation, the residue is diluted with 50 ml of water, taken up in ethyl acetate, washed with NaHCO$_3$ solution until neutral, concentrated and chromatographed over silica gel. The compound was characterized by the H NMR spectrum.

A number of compounds of the general formula I are listed as examples in Table 1 below.

TABLE 1

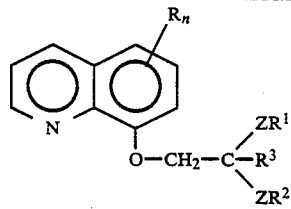

I

| Example No. | $R_n$ | Z | $R_1$ | $R_2$ | $R_3$ | m.p. [°C.] |
|---|---|---|---|---|---|---|
| 3. | H | O | $C_2H_5$ | $C_2H_5$ | H | |
| 4. | " | " | —CH$_2$—CH$_2$— | | H | |
| 5. | " | " | $C_2H_4OCH_3$ | $C_2H_4OCH_3$ | H | |
| 6. | 5-Cl | " | $CH_3$ | $CH_3$ | H | 86–90 |
| 7. | 5-Cl | O | —CH$_2$CH$_2$— | | H | 87–90 |
| 8. | " | " | —CH$_2$CH(n-C$_6$H$_{13}$)— | | H | 60–61 |
| 9. | 5-Cl | O | —CH$_2$C(CH$_3$)$_2$CH$_2$— | | H | 135–137 |
| 10. | " | " | n-C$_4$H$_9$ | n-C$_4$H$_9$ | H | |
| 11. | " | " | n-C$_8$H$_{17}$ | n-C$_8$H$_{17}$ | H | oil |
| 12. | " | " | —CH$_2$CH$_2$— | | CH$_3$ | oil |
| 13. | " | " | n-C$_4$H$_9$ | n-C$_4$H$_9$ | CH$_3$ | |
| 14. | " | " | CH$_2$—Ph | CH$_2$Ph | H | 109–110 |
| 15. | " | " | CH$_2$CH=CH$_2$ | CH$_2$CH=CH$_2$ | H | |
| 16. | " | " | $C_2H_4OCH_3$ | $C_2H_4OCH_3$ | H | oil |
| 17. | " | " | $C_2H_4OCH_3$ | $C_2H_5$ | H | " |
| 18. | " | " | CH$_2$CF$_2$CHFCF$_3$ | $C_2H_5$ | H | 34–39 |
| 19. | " | " | CH$_2$CH=CHC$_8$F$_{17}$(n) | $C_2H_5$ | H | oil |
| 20. | " | " | CH$_2$CCl$_3$ | CH$_2$CCl$_3$ | H | |

TABLE 1-continued

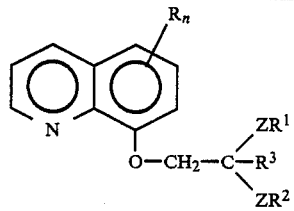

| Example No. | $R_n$ | Z | $R_1$ | $R_2$ | $R_3$ | m.p. [°C.] |
|---|---|---|---|---|---|---|
| 21. | " | " | $CH_2CH_2CH_2CH_2Cl$ | $CH_2CH_2CH_2CH_2Cl$ | H | oil |
| 22. | " | " | \multicolumn{2}{l|}{$-CH_2CH(CH_2CH_2CH_2CH_2Cl)$} | H | |
| 23. | " | " | \multicolumn{2}{l|}{$-CH_2CH(C_2H_4O-C_2H_5)$} | H | |
| 24. | " | " | \multicolumn{2}{l|}{$-CH_2CO-$} | H | |
| 25. | " | O/S | \multicolumn{2}{l|}{$-CH_2CH_2-$} | H | |
| 26. | " | S | $CH_2$ phenyl | $CH_2$ phenyl | H | |
| 27. | " | S | \multicolumn{2}{l|}{$-CH_2CH_2-$} | H | |
| 28. | N-oxide of 1 | | | | | oil |
| 29. | 5-Br | O | $C_2H_5$ | $C_2H_5$ | H | |
| 30. | " | O | n-$C_8H_{17}$ | n-$C_8H_{17}$ | H | |
| 31. | 5,7-$Cl_2$ | O | $C_2H_5$ | $C_2H_5$ | H | 38–40 |
| 32. | " | O | \multicolumn{2}{l|}{$-CH_2CH_2-$} | H | |
| 33. | N-oxide of 31 | | | | | |
| 34. | 2-$CH_3$ | O | $C_2H_5$ | $C_2H_5$ | H | oil |
| 35. | " | O | $C_2H_4OCH_3$ | $C_2H_4OCH_3$ | H | |
| 36. | 5,7-$Br_2$ | O | $C_2H_5$ | $C_2H_5$ | H | oil |
| 37. | 5,7-$Br_2$, 2-$CH_3$ | O | $C_2H_5$ | $C_2H_5$ | H | 70–71 |

C. BIOLOGICAL EXAMPLES

Example 1

Wheat and barley were raised in a greenhouse to the 3-4 leaf stage and then treated successively with the safeners according to the invention and a commercially available herbicide. The compounds were applied in the form of aqueous suspensions or emulsions. A few weeks after the treatment (wheat: 3 weeks, barely: 2 weeks), the extent of plant damage by the herbicide was assessed visually, the growth inhibition, in particular, being taken into account. The results from Table 2 show that the compounds according to the invention are able, even in the case of considerable overdosing of the herbicide, to greatly reduce severe damage in the crop plants and to completely eliminate less severe symptoms of damage. Mixtures of herbicides and compounds according to the invention are therefore suitable in an excellent fashion for selective combating of weeds in crop plants.

TABLE 2

| Compound | Dose kg/ha | Damage in % TA | Damage in % HV |
|---|---|---|---|
| Herbicide | 2.0 | 85 | — |
| $H_1$ | 0.2 | — | 90 |
| 1 + $H_1$ | 2.0 + 2.5 | 25 | — |
| | 0.2 + 2.5 | — | 20 |
| 31 + $H_1$ | 2.0 + 2.5 | 40 | — |
| | 0.2 + 2.5 | — | — |
| 7 + $H_1$ | 2.0 + 2.5 | 40 | — |
| | 0.2 + 2.5 | — | — |
| 28 + $H_1$ | 2.0 + 2.5 | 30 | — |
| | 0.2 + 2.5 | — | 40 |
| 12 + $H_1$ | 2.0 + 2.5 | 35 | — |
| | 0.2 + 2.5 | — | 70 |
| 11 + $H_1$ | 2.0 + 2.5 | 33 | — |

TABLE 2-continued

| Compound | Dose kg/ha | Damage in % TA | Damage in % HV |
|---|---|---|---|
| | 0.2 + 2.5 | — | 75 |
| 21 + $H_1$ | 2.0 + 2.5 | 40 | — |
| | 0.2 + 2.5 | — | 75 |
| 6 + $H_1$ | 2.0 + 2.5 | 10 | — |
| | 0.2 + 2.5 | — | 30 |
| 18 + $H_1$ | 2.0 + 2.5 | 20 | — |
| | 0.2 + 2.5 | — | 50 |
| 19 + $H_1$ | 2.0 + 2.5 | 45 | — |
| | 0.2 + 2.5 | — | 75 |
| 17 + $H_1$ | 2.0 + 2.5 | 30 | — |
| | 0.2 + 2.5 | — | 40 |
| 16 + $H_1$ | 2.0 + 2.5 | 25 | — |
| | 0.2 + 2.5 | — | 60 |
| 34 + $H_1$ | 2.0 + 2.5 | 30 | — |
| | 0.2 + 2.5 | — | — |
| 8 + $H_1$ | 2.0 + 2.5 | 40 | — |
| | 0.2 + 2.5 | — | 40 |
| 9 + $H_1$ | 2.0 + 2.5 | 40 | — |
| | 0.2 + 2.5 | — | 60 |

Abbreviations:
$H_1$ = fenoxaprop-ethyl (ethyl 2-[4-(6-chlorobenzoxazolyloxy)-phenoxy]-propionate)
TA = *Triticum aestivum* (wheat)
HV = *Hordeum vulgare* (barley)

Example 2

Cereals and weed grasses were raised under optimum growth conditions in a greenhouse to the 3-4 leaf stage and treated with mixtures of the compounds according to the invention and herbicides. The preparations were applied in the form of aqueous suspensions or emulsions. 3-4 weeks after application, the test plants were assessed visually for growth changes and damage compared to untreated controls or controls treated with the herbicides alone. The results from Table 3 show that the compounds according to the invention are able to effectively prevent damage on crop plants without impairing the herbicidal action against weed grasses.

TABLE 3

Safener action of the compounds according to the invention in wheat and oat grass

| Compound | Dose kg/ha | Damage in % TA | AVF |
|---|---|---|---|
| H₁ | 2.0 | 40 | — |
|  | 0.3 | — | 100 |
| H₁ + 1 | 2.0 + 1.0 | 15 | — |
|  | 2.0 + 0.25 | 10 | — |
|  | 0.3 + 1.0 | — | 100 |
|  | 0.3 + 0.25 | — | 100 |

Abbreviation: AVF = *Avena fatua* (oat grass)

I claim:

1. A herbicidal agent which contains a herbicide selected from the group consisting of carbamates, thiocarbamates, haloacetanilides, substituted phenoxy-, naphthoxy- and phenoxyphenoxy-carboxylic acid derivatives, heteroaryloxyphenoxycarboxylic acid derivatives and dimedone oxime derivatives and an antidote compound of the formula I wherein the individual radicals have the following meaning:

R is halogen or $(C_1-C_4)$alkyl,

Z, in each case independently of one another, is O or S, $R^1$ and $R^2$, independently of one another, is H, $(C_1-C_8)$ alkyl, $(C_3-C_8)$ alkenyl, $(C_1-C_4)$alkoxy-$(C_1-C_4-)$alkyl, $(C_1-C_{12})$ haloalkyl having up to 17 halogen atoms, $(C_3-C_{12})$ haloalkenyl having 17 halogen atoms or phenyl-$(C_1-C_2)$ alkyl, $R^3$ is H or $(C_1-C_4)$ alkyl, and n is 0, 1 or 2, and the salt and N-oxides thereof, in a ratio by weight of (0.01–10):1 of compound of formula I to herbicide.

2. The herbicidal agent as claimed in claim 1, wherein R is halogen, Z is oxygen, $R^1$ and $R^2$ are $(C_1-C_4)$ alkyl or $(C_1-C_2)$alkoxy-$(C_1-C_2)$ alkyl, $R^3$ is hydrogen and n is 1 or 2.

3. A herbicidal agent as claimed in claim 1, wherein the antidote is 5-chloroquinol-8-yloxyacetaldehyde di-ethyl acetal.

4. A herbicidal agent as claimed in claim 1, wherein the herbicide is selected from the group consisting of the carbamates, thiocarbamates, haloacetanilides, phenoxy-, naphthoxy-, phenoxyphenoxy-, quinolyloxphenoxy-, quinoxalyloxyphenoxy-, pyridyloxyphenoxy-, benzoxazolyl-oxyphenoxy-and benzothiazolyloxyphenoxy-carboxylic acid derivatives.

5. A herbicidal agent as claimed in claim 1, wherein the herbicide is fenoxaprop-ethyl.

6. A process for protecting crop plants against phytotoxic side effects of herbicides, selected from the group consisting of carbamates, thiocarbamates, haloacetanilides, substituted phenoxy-, naphthoxy- and phenoxyphenoxy-carboxylic acid derivatives, heteroaryloxyphenoxycarboxylic acid derivatives and dimedone oxime derivatives wherein the plants, parts of plants or nutritive substrata of plants are treated with an effective amount of a compound of the formula I wherein the individual radicals have the following meaning:

R is halogen or $(C_1-C_4)$alkyl,

Z, in each case independently of one another, is O, or S, $R^1$ and $R^2$, independently of one another, is H, $(C_1-C_8)$ alkyl, $(C_3-C_8)$ alkenyl, $(C_1-C_4)$alkoxy-$(C_1-C_4-)$alkyl, $(C_1-C_{12})$ haloalkyl having up to 17 halogen atom, $(C_3-C_{12})$ haloalkenyl having up to 17 halogen atoms or phenyl-$(C_1-C_2)$ alkyl, $R^3$ is H or $(C_1-C_4)$ alkyl, and n is 0, 1 or 2, and the salts and N-oxides thereof.

7. The process as claimed in claim 6, wherein an effective amount of the compound of the formula I is applied in combination with a herbicide from the group consisting of carbamates, thiocarbamates, haloacetanilides, phenoxy-, naphthoxy-, phenoxyphenoxy-, quinolyloxphenoxy-, quinoxalyloxy-phenoxy-, pyridyloxphenoxy-, benzoxazolyloxyphenoxy-and benzothiazolyloxphenoxy-carboxylic acid derivatives.

8. A process as claimed in claim 6, wherein the herbicide is fenoxaprop-ethyl.

9. The process as claimed in claim 6, wherein the plant-protecting agents and the herbicides are applied in the ratio (0.01–10):1.

10. A compound of the formula I wherein the individual radicals have the following meaning:

R is halogen or $(C_1-C_4)$alkyl,

Z, in each case independently of one another, is O or S, $R^1$ and $R^2$, independently of one another, is H, $(C_1-C_8)$ alkyl, $(C_3-C_8)$ alkenyl, $(C_1-C_4)$-alkoxy-$(C_1-C_4-)$alkyl, $(C_1-C_{12})$ haloalkyl having up to 17 halogen atoms, $(C_3-C_{12})$ haloalkenyl having up to 17 halogen atoms or phenyl-$(C_1-C_2)$ alkyl, $R^3$ is H or $(C_1-C_4)$ alkyl, and n is 0, 1 or 2, and the salts and N-oxides thereof with the exception of 8-quinolyloxy-acetaldehyde di-ethyl acetal.

11. A compound of the formula I as defined in claim 10, wherein R is halogen, Z is oxygen, $R^1$ and $R^2$ are $(C_1-C_4)$ alkyl or $(C_1-C_2)$alkoxy-$(C_1-C_2)$alkyl, $R^3$ is hydrogen and n is 1 or 2.

12. A herbicidal agent containing fenoxaprop-ethyl and an antidote of the formula I

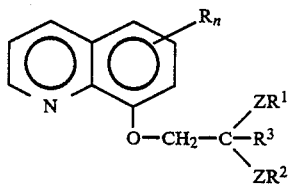

wherein the individual radicals have the following meaning:

R is haloen or $(C_1–C_4)$alkyl,

Z, in each case independently of one another, is O or S, $R^1$ and $R^2$ independently of one another, is H, $(C_1–C_8)$ alkyl, $(C_3–C_8)$ alkenyl, $(C_1–C_4)$alkoxy-$(C_1–C_4-)$alkyl, $(C_1–C_{12})$ haloalkyl having up to 17 halogen atom, $(C_3–C_{12})$ haloalkenyl having up to 17 halogen atoms or phenyl-$(C_1–C_2)$ alkyl, or $R^1$ and $R^2$ together are a di-, tri- or tetramethylene chain which is optionally substituted by up to two $(C_1–C_8)$alkyl, $(C_1–C_4)$ haloalkyl or $(C_1–C_4)$ alkoxy-$(C_1–C_4)$alkyl groups and/or by an oxo group, $R^3$ is H or $(C_1–C_4)$ alkyl, and n is 0, 1 or 2, and the salts and N-oxides thereof, in a ratio by weight of (0.01–10).

* * * * *